(12) United States Patent
Qi et al.

(10) Patent No.: US 9,976,942 B2
(45) Date of Patent: May 22, 2018

(54) CRYOGENIC TISSUE SAMPLE EMBEDDING STORAGE SYSTEM

(71) Applicant: THE FIRST HOSPITAL OF CHINA MEDICAL UNIVERSITY, Shenyang, Liaoning (CN)

(72) Inventors: Ruiqun Qi, Liaoning (CN); Xinghua Gao, Liaoning (CN); Hongduo Chen, Liaoning (CN)

(73) Assignee: THE FIRST HOSPITAL OF CHINA MEDICAL UNIVERSITY, Shenyang, Liaoning (CN)

( * ) Notice: Subject to any disclaimer, the term of this patent is extended or adjusted under 35 U.S.C. 154(b) by 0 days. days.

(21) Appl. No.: 15/433,925

(22) Filed: Feb. 15, 2017

(65) Prior Publication Data
US 2017/0268969 A1 Sep. 21, 2017

(30) Foreign Application Priority Data
Mar. 21, 2016 (CN) .......................... 2016 1 0159556

(51) Int. Cl.
| | | |
|---|---|---|
| G01N 1/00 | (2006.01) | |
| G01N 1/42 | (2006.01) | |
| B65D 25/02 | (2006.01) | |
| G01N 1/36 | (2006.01) | |

(52) U.S. Cl.
CPC ............... G01N 1/42 (2013.01); B65D 25/02 (2013.01); G01N 1/36 (2013.01)

(58) Field of Classification Search
CPC ................................... G01N 1/00; G01N 1/42
See application file for complete search history.

(56) References Cited

U.S. PATENT DOCUMENTS 7,156,814 B1 * 1/2007 Williamson, IV . A61B 10/0096
435/297.5

* cited by examiner

*Primary Examiner* — Jyoti Nagpaul
(74) *Attorney, Agent, or Firm* — Kile Park Reed & Houtteman PLLC (57) ABSTRACT

A cryogenic tissue sample embedding storage system belongs to the field of cryopreservation of biological tissue samples, which in particular, relates to a cryogenic tissue sample embedding storage system. The present invention provides a cryogenic tissue sample embedding storage system that can avoid the confusion of samples, prevent damage to identifier information in the cutting process, and has high embedding efficiency. The present invention comprises an embedded label, a label cover, and an embedding base, and in terms of its structure, the embedding base is provided with a groove structure for placing and limiting the position of the embedded label, and an embedding enclosure wall flexibly connected to the embedding base is disposed above the groove structure.

9 Claims, 6 Drawing Sheets

CRYOGENIC TISSUE SAMPLE EMBEDDING STORAGE SYSTEM

TECHNICAL FIELD

The present invention relates to the field of cryopreservation of biological tissue samples, and in particular, to a cryogenic tissue sample embedding storage system.

BACKGROUND ART

In bioscience-related fields, researchers are often confronted with the problem of cryopreservation of biological samples. There are various types of biological samples, and in terms of physical states, the samples may be classified into gaseous samples, for example, expired air; liquid samples, for example, body fluids such as blood, urine, cerebrospinal fluid, tears, and saliva; and solid samples, for example, various biological tissues. Apart from that, the cryogenic freezing method is used in many fields such as agriculture, chemical engineering, archaeology and geological prospecting to preserve various precious sample data.

In the field of bioscience, when a solid tissue sample needs to be preserved, a common method at present is to place the tissue into a cryogenic vial for cell cryopreservation, label the cryogenic vial and then put the cryogenic vial into a refrigerator at −80 degrees centigrade, or directly place the tissue into liquid nitrogen for cryopreservation. Another method is to place the tissue on a metal cryogenic tray, and then add an opti-mum cutting temperature compound (OCT) or a shaping agent of another type dropwise around the specimen, where the shaping agent is generally liquid at a normal temperature, and becomes solid in a cryogenic environment. The function of the shaping agent is to protect the specimen from air drying and deformation, and guarantee the isolation of the specimen, and more importantly, the shaping agent can carry the specimen when operations such as freezing sectioning are performed on the specimen in the future. In the latter method, to make the shape of the embedded sample regular, some people use a plastic apparatus of a specified shape for shaping.

A disadvantage of the existing embedding means lies in that: after a sample which is directly cryopreserved by using a cell cryogenic vial is taken out, it needs to be re-embedded before use; and if the shape and size are not suitable, it is extremely difficult to make adjustment in a freezing condition.

After samples preserved using the foregoing two methods are taken out, no unique specimen identifier can be reserved on the surface of the sample. Once a misoperation occurs, the samples are easily confused with each other; the samples are no longer associated with sample-containing sealed bags and cryogenic vials that carry the sample information identifiers; and it is difficult to restore the association, causing the samples to be confused. Such a risk causes a disastrous consequence for subsequent use and results in disuse of the samples.

In addition, the current embedding operation method is relatively complex, where operations need to be performed on each sample separately, rather than operation in batches, which is time-consuming and energy-consuming, causes a waste of embedding materials, is difficult to standardize, and is not good for recycling of samples or the dynamic integration with a modern sample repository management system.

Secondly, an OCT-embedded specimen has an irregular shape, which makes regular placement and storage difficult; the OCT-embedded specimen occupies large refrigeration space, and a large amount of energy and resources are consumed to maintain a low temperature.

In practical application, for a layered tissue having envelope, epithelium and deep tissue structures, it is generally necessary to cut off a section from which structures of several layers can be seen at the same time, and the tissue direction thereof needs to be identified during operations such as slicing. For example, human skin has a cuticle surface exposed to air, and also has a subcutaneous tissue in another direction. During practical application, layers from the outside to the inside need to be observed at the same time, and if a section parallel to the surface of the skin is used mistakenly, indexes that need to be observed and studied cannot be obtained. However, after the opaque shaping agent is used for embedding, the internal structure is unrecognizable.

An auxiliary shaping device is used at present, which slightly improves the shape, but still fails to implement the function of providing an inseparable label on a specimen, and still fails to avoid the prominent problems of misoperation on specimens, confusion between specimens, and the waste of specimens.

An operation environment of OCT embedding is generally a cold cavity of a freezing microtome, a cryogenic refrigerator or a liquid nitrogen cup placed in a room-temperature environment. The cold cavity of the freezing microtome has an irregular shape and small space, which makes the operation extremely inconvenient. When the operation is performed in the cryogenic refrigerator, the refrigerator needs to be open and closed repeatedly, which is not only inconvenient but also very harmful to the refrigerator. The liquid nitrogen refrigeration involves dangerous and complex operations, and also wastes a large amount of liquid nitrogen resources.

SUMMARY OF THE INVENTION

In view of the aforementioned problems, the present invention provides a cryogenic tissue sample embedding storage system that can avoid confusing samples, prevent identifier information from being damaged in a cutting process, and has high embedding efficiency.

To achieve the foregoing objective, the present invention uses the following technical solution: the present invention comprises an embedded label, a label cover, and an embedding base, where in terms of its structure, the embedding base is provided with a groove structure for placing and limiting the position of the embedded label, and an embedding enclosure wall flexibly connected to the embedding base is disposed above the groove structure.

As a preferred solution, the embedded label of the present invention is provided with an electronic scanning identification code.

As another preferred solution, the embedded label of the present invention comprises an enclosure frame, where the lower end of the enclosure frame is provided with a bearing bottom plate, and a side wall in the enclosure frame is provided with a vertical inverted-L-shaped hook-like portion.

As another preferred solution, both the enclosure frame and the bearing bottom plate of the present invention are square; the label cover is a square barrel, the upper end of the square barrel is a roof, and the roof is provided with a through hole.

As another preferred solution, the bearing bottom plate of the present invention is provided with an upright column, and the upper end of the upright column is provided with a hook-like portion which is horizontally bent.

As another preferred solution, the bearing bottom plate of the present invention is flexibly connected to the enclosure frame, and one side of the bearing bottom plate is connected to the enclosure frame through an elastic strip; the bearing bottom plate is provided with a connection plug column, and the lower end of the enclosure frame is provided with a first connection plug hole corresponding to the connection plug column.

As another preferred solution, in the present invention, there are a plurality of groove structures, which are evenly distributed horizontally; and the groove structure is a vertical square groove with one side open.

As another preferred solution, the embedding enclosure wall of the present invention comprises comb-like bodies that are disposed oppositely, and an intersecting portion of the two comb-like bodies forms an embedding limiting area; the comb-like body is provided with a vertical through hole, a connection plug rod is inserted in the vertical through holes, and the embedding base is provided with a second connection plug hole corresponding to the lower end of the connection plug rod; and the lower end of the embedding enclosure wall is provided with a prying gap.

As another preferred solution, the embedding base of the present invention is provided with a cooling ventilation duct; and the embedding base and the embedding enclosure wall utilize heat-conducting metal.

As another preferred solution, the present invention further comprises a label placement box for containing the embedded label, where a plurality of staggered horizontal thin flexible plastic spacers and vertical thin flexible plastic spacers are disposed in the label placement box, and the lower end of the plastic spacer is adhesively bonded with the bottom surface of the placement box; the label cover is covered on the embedded label, the upper end of the label cover is disposed at the bottom end of a placement area enclosed by the plastic spacers, and the embedded label is disposed at the upper end of the placement area; the lower end of the horizontal thin flexible plastic spacer is provided with a lower connection slot, the upper end of the vertical thin flexible plastic spacer is provided with an upper connection slot, and the horizontal thin flexible plastic spacer is connected downward to the vertical thin flexible plastic spacer through the lower connection slot and the upper connection slot.

The present invention has the following beneficial effects:

Once the embedded labels of the present invention are embedded, the labels are always (while the specimens are used) associated with the specimen, and the labels can firmly carry unique identifier information of the specimens, so that samples are not confused even if a misoperation such as sample dropping or scattering occurs.

The embedding base of the present invention is provided with the groove structures for placement of the embedded labels and for limiting the positions of the embedded labels, and an embedding enclosure wall flexibly connected to the embedding base is disposed above the groove structures, so that the shape of the combination of the embedded tissue and the embedded label can be limited, and the identifier information is not damaged at all during a cutting process. Moreover, storage space is saved while the identifier information of the sample is carried firmly, without affecting adhering between an embedded block and a microtome during subsequent freezing sectioning, or cutting of the tissue by a microtome knife (where the blade does not touch the embedded label). After sectioning, a regular preservation state can still be restored reversibly.

The present invention can implement batch operations, thereby significantly saving time and labor and improving efficiency.

The present invention makes full use of the embedding agent, and effectively avoids the loss of the conventional irregular terrace-like OCT embedding agent. Meanwhile, the embedding block is rendered in a regular and uniform shape, facilitating regular storage, significantly saving storage space, and reducing cost in hardware and energy consumption of cryopreservation.

BRIEF DESCRIPTION OF THE DRAWINGS

The present invention is further described with reference to the accompanying drawings and detailed description. The protection scope of the present invention is not limited to the description of the following content.

In the figures, 1 represents an enclosure frame; 2 represents an elastic strip; 3 represents a bearing bottom plate; 4 represents a hook-like portion; 5 represents an upright column; 6 represents a connection plug column; 7 represents an inverted-L-shaped hook-like portion; 8 represents a first connection plug hole; 9 represents a square groove; 10 represents a comb-like body; 11 represents a connection plug rod; 12 represents a through hole; 13 represents a label cover; 14 represents a rigid plastic partition; 15 represents an upper connection slot; 16 represents a horizontal thin flexible plastic spacer; 17 represents a vertical thin flexible plastic spacer; 18 represents a grid-shaped embedding liquid infiltrating hole; 19 represents a label sheet; 20 represents a clamping block; and 21 represents a protruding portion.

DETAILED DESCRIPTION

As shown in the figures, the present invention comprises embedded labels, label covers 13 and an embedding base, where the embedding base is provided with a plurality of groove structures for placement of the embedded labels and for limiting the positions of the embedded labels, and an embedding enclosure wall flexibly connected to the embedding base is disposed above the groove structures.

Figure 1:
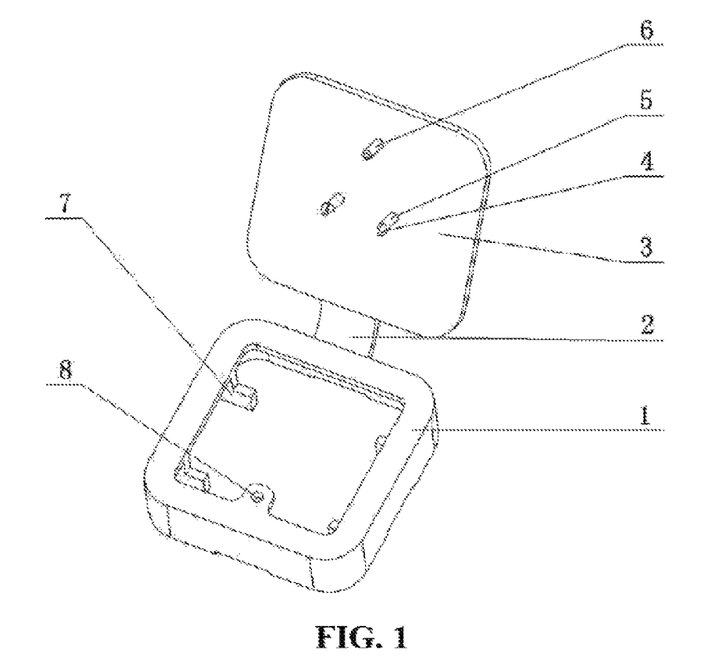
FIG. 1 is a schematic structural diagram of an embedded label according to the present invention.

The embedded label is provided with an electronic scanning identification code, to facilitate modern electronic batch scanning identification.

The embedded label comprises an enclosure frame 1, where the lower end of the enclosure frame 1 is provided with a bearing bottom plate 3, and a side wall in the enclosure frame 1 is provided with vertical inverted-L-shaped hook-like portions 7. The enclosure frame 1 can prevent an embedding liquid from flowing out, and the inverted-L-shaped hook-like portions 7 can make the embedded label more firmly bonded with the tissue to be embedded and the frozen embedding liquid.

Both the enclosure frame 1 and the bearing bottom plate 3 are square.

The bearing bottom plate 3 is provided with upright columns 5, and the upper end of each upright column 5 is provided with a hook-like portion 4 which is horizontally bent. The hook-like portion 4 can make the embedded label more firmly bonded with the tissue to be embedded and the frozen embedding liquid, and prevent the embedded label from falling off.

Figure 2:
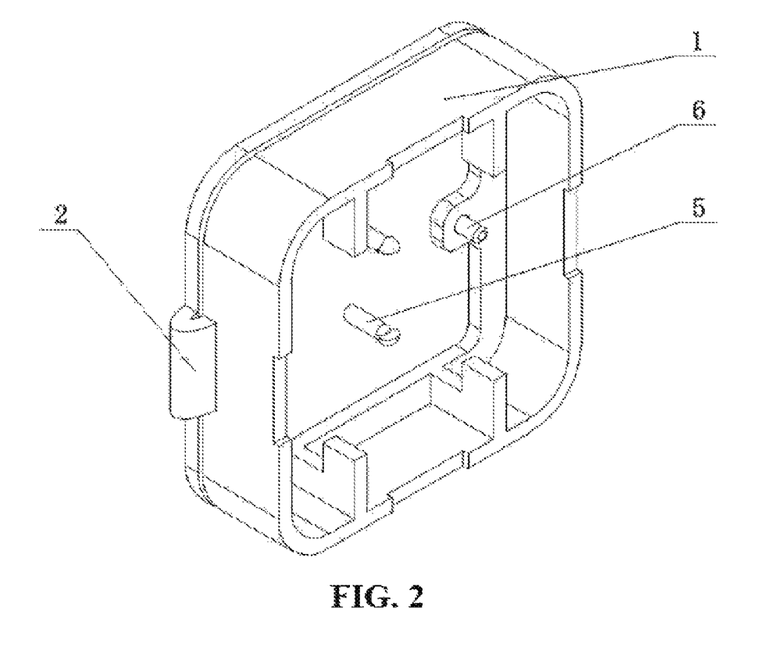
FIG. 2 is a schematic structural diagram of an embedded label after being clamped according to the present invention.

The bearing bottom plate 3 and the enclosure frame 1 are flexibly connected, and one side of the bearing bottom plate 3 is connected to the enclosure frame 1 through an elastic strip 2. The bearing bottom plate 3 is provided with a connection plug column 6, and the lower end of the enclosure frame 1 is provided with a first connection plug hole 8 corresponding to the connection plug column 6.

Figure 4:
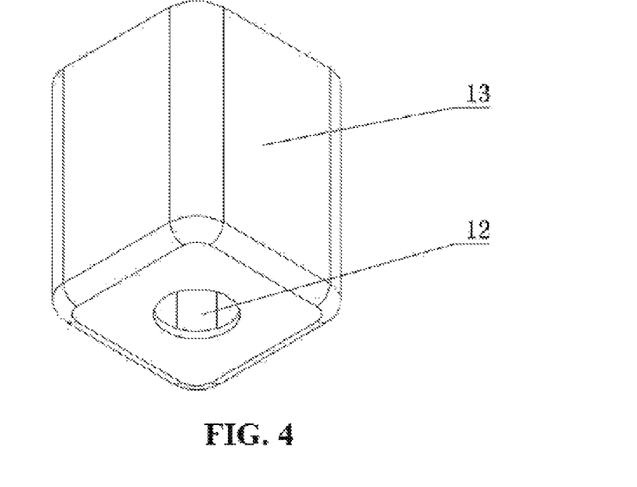
FIG. 4 is a schematic structural diagram of a label cover according to the present invention.
Figure 5:
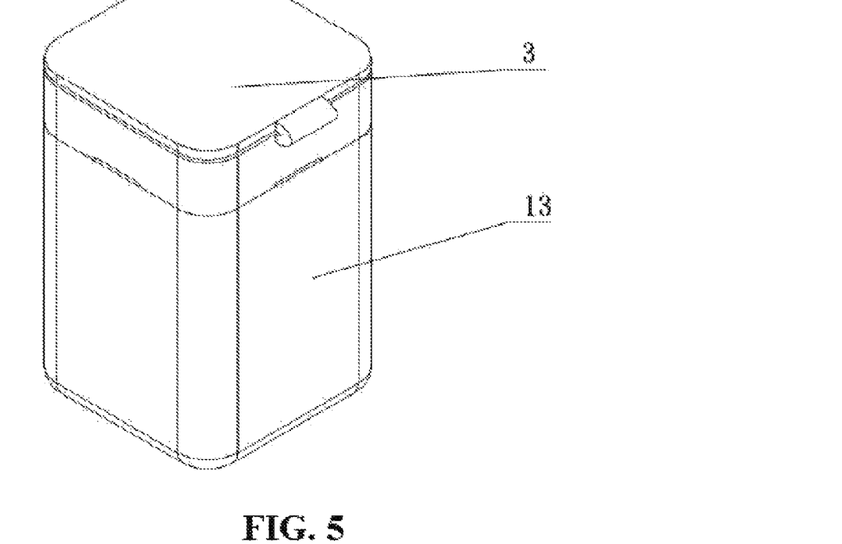
FIG. 5 is a schematic structural diagram of a combination of a label cover and an embedded label according to the present invention.

The label cover 13 is a square barrel, the upper end of the square barrel is a roof, and the roof is provided with a through hole 12. A rod-like component may be used to eject the embedded tissue via the through hole 12, to facilitate separation of the embedded tissue and the embedded label from the label cover 13.

Both the embedded label and the label cover 13 are made of plastic.

Figure 3:
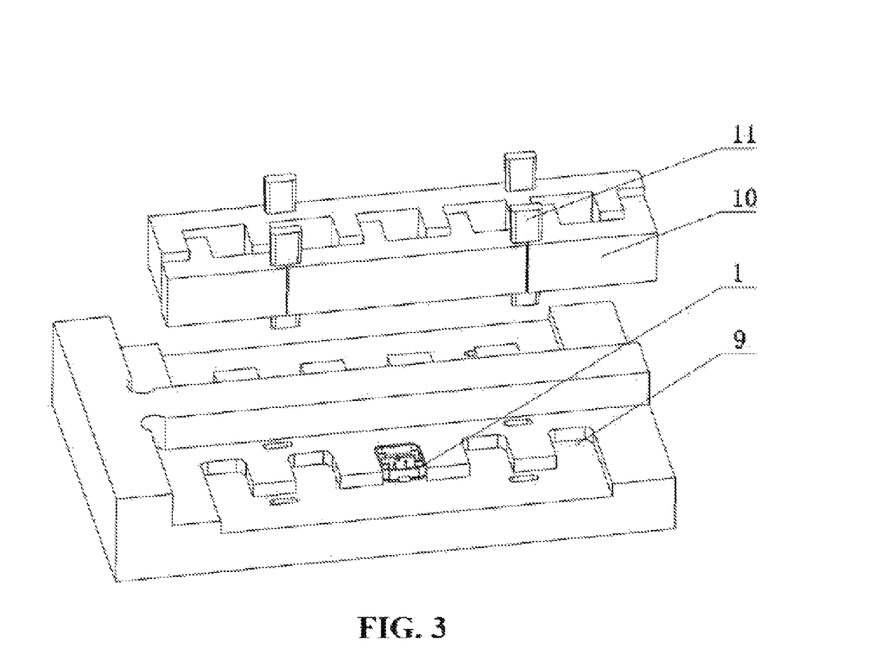
FIG. 3 is a schematic structural diagram of an embedding base and an embedding enclosure wall according to the present invention.

The plurality of groove structures are provided, which are evenly distributed horizontally, and each groove structure is a vertical square groove 9 with one side open. One side of the square groove 9 is open so that a connection body of the embedded tissue and the embedded label can slide out of the square groove 9. When the embedded label is put into the vertical square groove 9, the lower end surface of the bearing bottom plate 3 abuts against the bottom surface of the vertical square groove 9.

The embedding enclosure wall comprises comb-like bodies 10 that are disposed opposite to each other, and an intersecting portion of the two comb-like bodies 10 forms an embedding limiting area. Each comb-like body 10 is provided with vertical through holes, connection plug rods 11 are inserted in the vertical through holes, and the embedding base is provided with second connection plug holes corresponding to the lower ends of the connection plug rods 11.

Each connection plug rod 11 is a conical connection plug rod 11, thereby being stably connected.

The embedding base is provided with a filing structure, so as to grind the embedded tissue.

The lower end of the embedding enclosure wall is provided with a prying gap. By providing the prying gap, a pry bar may be inserted into the prying gap to pry the embedding enclosure wall, so as to separate the embedding enclosure wall from the embedding base.

The embedding base is provided with a cooling ventilation duct. Cooling air may be blown into the cooling ventilation duct, to implement rapid cooling of the embedding base. By providing the cooling ventilation duct, biological information (such as DNA, RNA and protein) in the specimen is preserved more desirably (with a faster freezing process, biomolecules are less likely to degrade).

Figure 6:
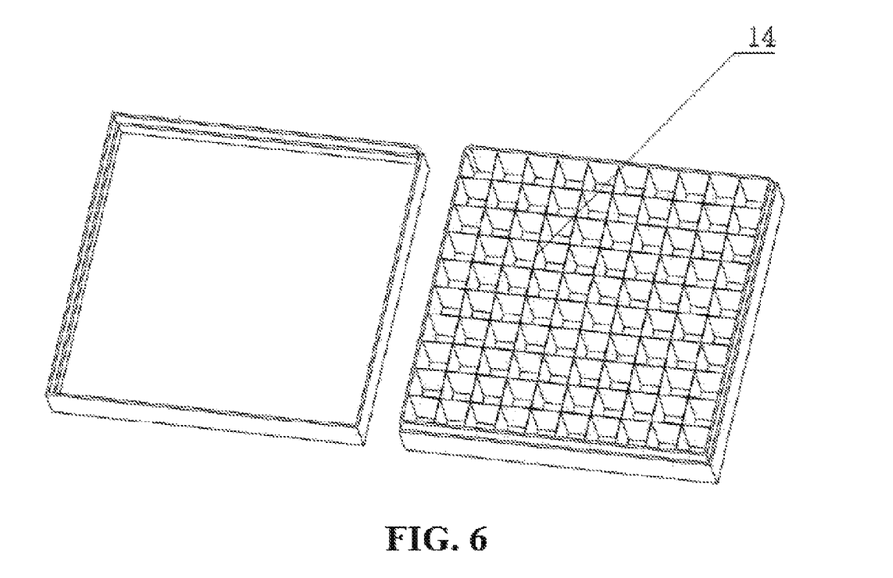
FIG. 6 is a schematic structural diagram of an existing embedded-tissue placement box according to the present invention.
Figure 7:
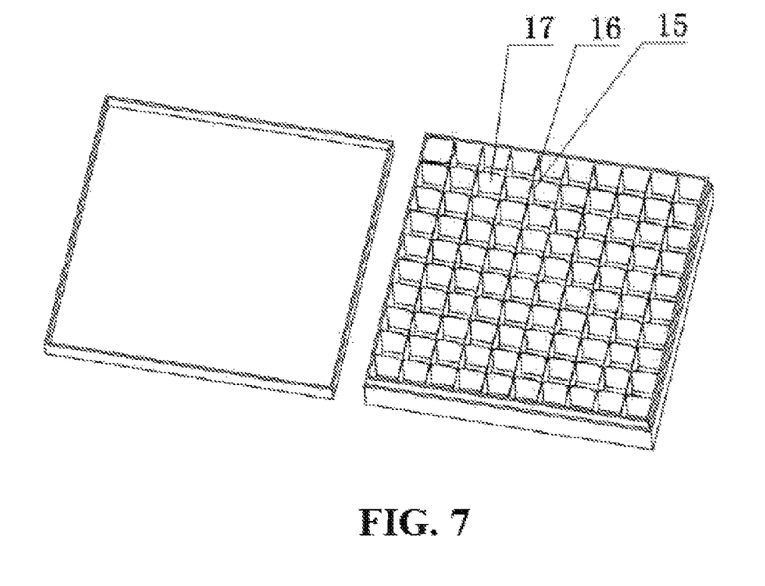
FIG. 7 is a schematic structural diagram of a label placement box according to the present invention.

The present invention further comprises a label placement box for containing the embedded labels, where a plurality of staggered horizontal thin flexible plastic spacers 16 and vertical thin flexible plastic spacers 17 are disposed in the label placement box, and the lower ends of the plastic spacers are adhesively bonded with the bottom surface of the placement box. The label cover 13 is covered on the embedded label, the upper end of the label cover 13 is disposed at the bottom end of the placement area enclosed by the plastic spacers, and the embedded label is disposed at the upper end of the placement area. A rigid plastic partition 14 is used in an existing embedded-tissue placement box, and with a same overall dimension, the existing embedded-tissue placement box contains less embedded tissues compared with the label placement of the present invention. The height of the label placement box of the present invention may be set to ⅓ of the height of the existing embedded-tissue placement box, whereas the existing embedded-tissue placement box is excessively high and it is inconvenient to pick and place embedded tissues.

In the present invention, there is no connection component between the label cover 13 and the embedded label, the label cover 13 is merely covered on the embedded label, the embedded tissue is placed in the label cover 13, and the inner wall of the label cover 13 is adhesively bonded with the cooled embedding liquid. The label cover 13 can prevent the solidified embedding liquid from melting or evaporating.

The label placement box is made of paper.

The lower end of the horizontal thin flexible plastic spacer 16 is provided with a lower connection slot, the upper end of the vertical thin flexible plastic spacer 17 is provided with an upper connection slot 15, and the horizontal thin flexible plastic spacer 16 is connected downward to the vertical thin flexible plastic spacer 17 through the lower connection slot and the upper connection slot 15. Use of a cross slot can reduce the thickness of the spacer, so that more spaces can be provided.

The cryogenic tissue sample embedding storage system may be disposed in a cryogenic operation box, and one side of the cryogenic operation box may be provided with an operation opening. A dedicated freezing space suitable for operation may be provided according to operating habits of a human body, which improves operation convenience, and makes freezing embedding possible for users who have neither a microtome nor liquid nitrogen.

The embedding base and the embedding enclosure wall are made of heat-conducting metal. In the conventional cooling method, cooling relies on ordinary physical conduction, while the present invention can accelerate cooling of the specimen by using the heat-conducting metal body.

Figure 8:
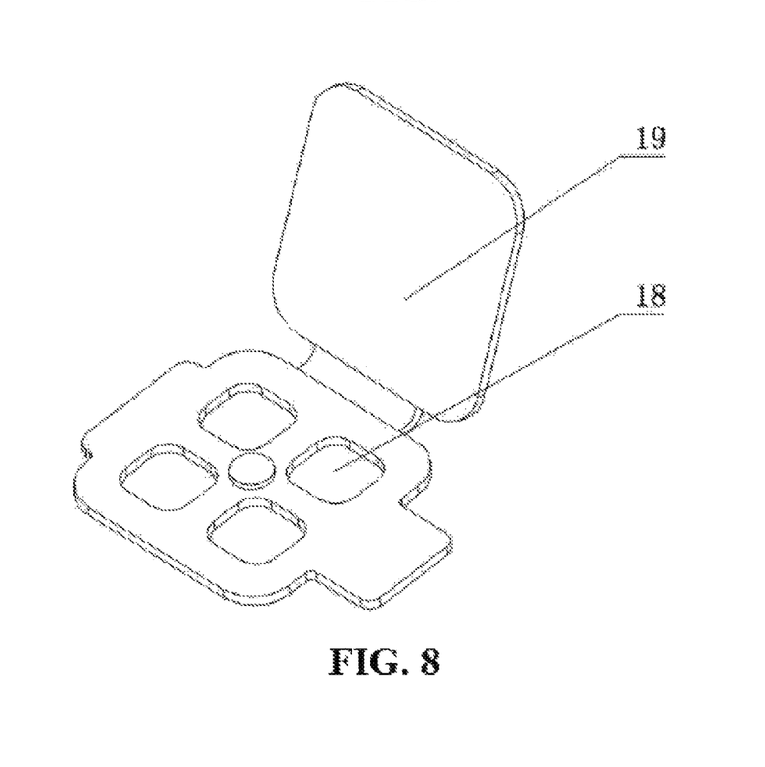
FIG. 8 is a schematic structural diagram of a first-generation embedded label according to the present invention.

The present invention is an optimal solution obtained after a large quantity of experiments over a long period of time, and a development process of the present invention is briefly described below:

A first-generation embedded label comprises a bottom embedded sheet and an upper label sheet 19, wherein the embedded sheet and the label sheet 19 are connected through a connection sheet on one side, the embedded sheet comprises a grid-shaped embedding liquid infiltrating hole 18, and the embedded sheet may be connected to a tissue to be embedded, but the bottom of the embedded sheet is too shallow to provide firm embedding. In addition, the connection sheet is highly elastic, and cannot be adhesively bonded with the embedding liquid easily. One side of the bottom embedded sheet is provided with a horizontally extending portion to be held by hands respectively.

Figure 9:
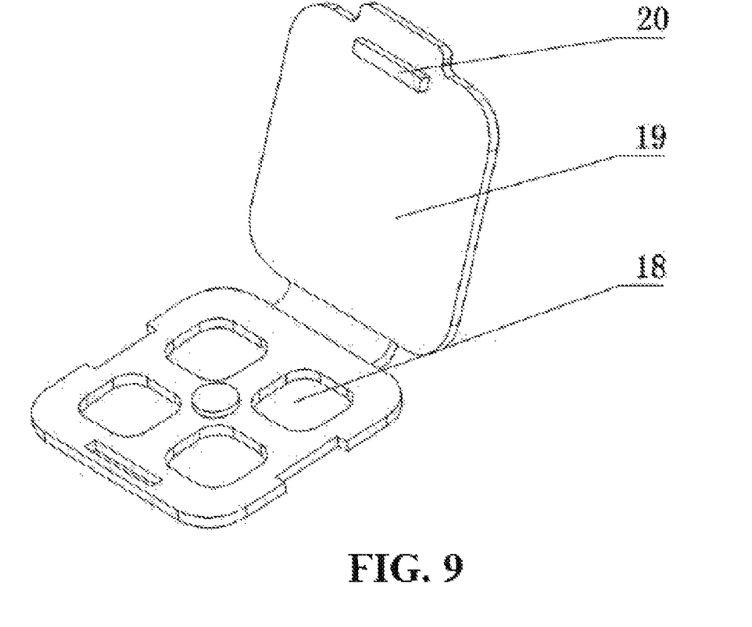
FIG. 9 is a schematic structural diagram of a second-generation embedded label according to the present invention.

Based on the first-generation embedded label, in a second-generation embedded label, the bottom embedded sheet is provided with a clamping groove, and the label sheet 19 is provided with a clamping block 20 corresponding to the clamping groove; the connection sheet is set to be thinner, which facilitates clamping, but is easily damaged. Two sides of the embedded sheet are provided with clamping grooves, to facilitate clamping between the embedded sheet and the label cover 13.

Figure 10:
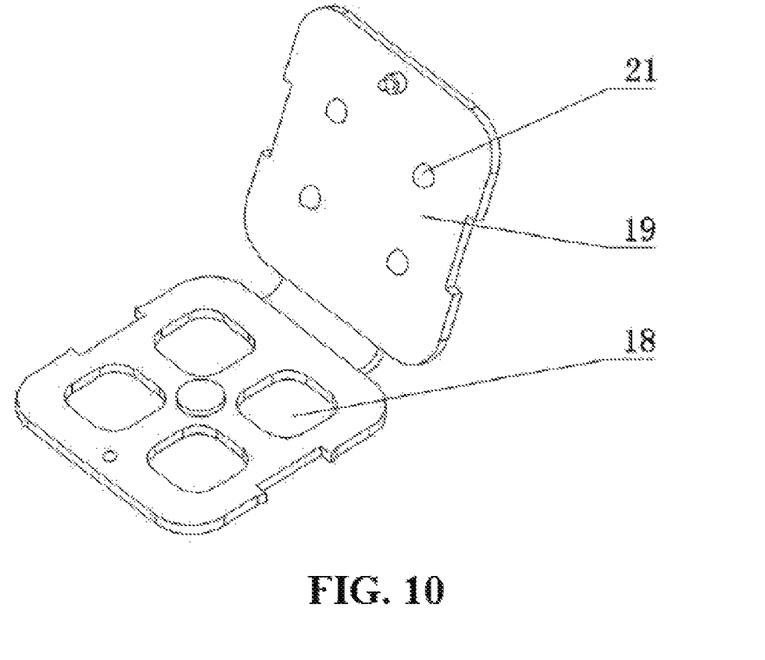
FIG. 10 is a schematic structural diagram of a third-generation embedded label according to the present invention.

Based on the second-generation embedded label, in a third-generation embedded label, corresponding to an area of the infiltrating hole on the embedded sheet, the label sheet 19 is provided with a tapered protruding portion 21 that enhances an embedding bonding force.

Figure 11:
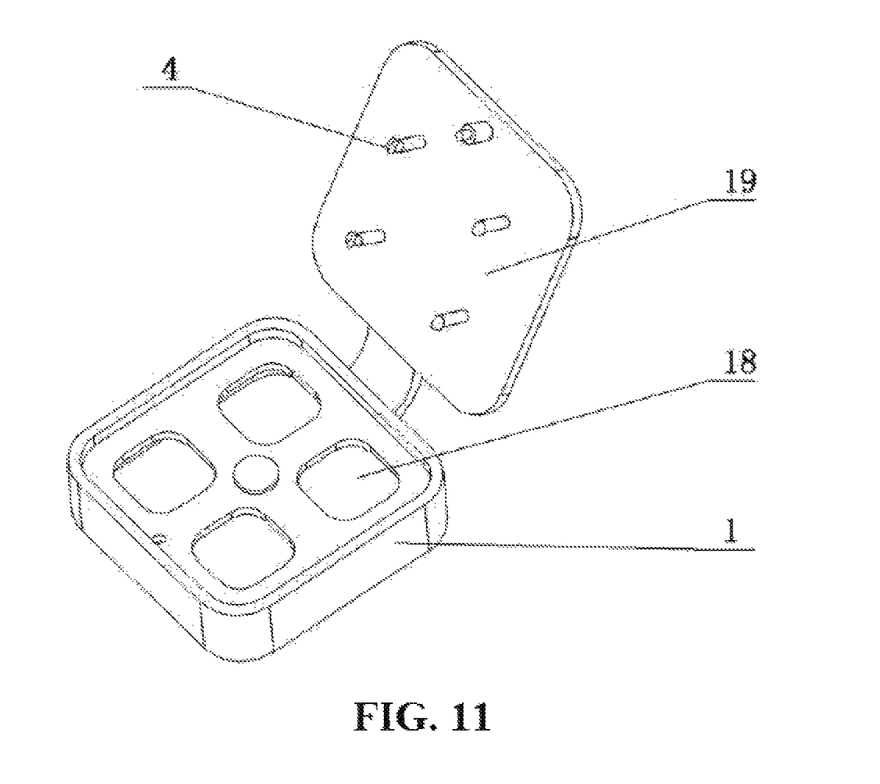
FIG. 11 is a schematic structural diagram of a fourth-generation embedded label according to the present invention.

Based on the third-generation embedded label, in a fourth-generation embedded label, an enclosure frame 1 is added on the periphery of the embedded sheet, where the enclosure frame 1 has a certain thickness and is bonded with the embedded sheet; when the embedded label is disposed in a groove of the embedding base, the enclosure frame 1 has a limiting function, preventing the embedded label from moving to the left and right, and making operations stable. A hook-like portion 4 is disposed at the front end of the protruding portion 21, to enhance the embedding bonding force.

The present invention is a fifth-generation embedded label, in which the grid-shaped embedding liquid infiltrating hole 18 is replaced with an opening structure, because a cross structure of the grid-shaped embedding liquid infiltrating hole 18 has a weak bonding and fixing effect on the embedded ice as it is difficult for the embedding liquid to fill up the bottom.

It can be understood that, the foregoing specific description about the present invention is merely used to illustrate the present invention but is not limited to the technical solutions described in the embodiments of the present invention. A person of ordinary skill in the art should understand that, modifications or equivalent replacements can still be made to the present invention to achieve the same technical effect, and any modification or equivalent replacement that meets the usage requirement falls in the protection scope of the present invention.

What is claimed is:

1. A cryogenic tissue sample embedding storage system, comprising:
    an embedded label;
    a label cover;
    an embedding base, wherein in terms of its structure, the embedding base is provided with a groove structure for placing and limiting the position of the embedded label, and an embedding enclosure wall flexibly connected to the embedding base is disposed above the groove structure; and
    a label placement box for containing the embedded label, wherein a plurality of staggered horizontal thin flexible plastic spacers and vertical thin flexible plastic spacers are disposed in the label placement box, and the lower end of the plastic spacer is adhesively bonded with the bottom surface of the placement box; the label cover is covered on the embedded label, the upper end of the label cover is disposed at the bottom end of a placement area enclosed by the plastic spacers, and the embedded label is disposed at the upper end of the placement area; the lower end of the horizontal thin flexible plastic spacer is provided with a lower connection slot, the upper end of the vertical thin flexible plastic spacer is provided with an upper connection slot, and the horizontal thin flexible plastic spacer is connected downward to the vertical thin flexible plastic spacer through the lower connection slot and the upper connection slot.

2. The cryogenic tissue sample embedding storage system of claim 1, wherein the embedded label is provided with an electronic scanning identification code.

3. The cryogenic tissue sample embedding storage system of claim 1, wherein the embedded label comprises an enclosure frame, the lower end of the enclosure frame is provided with a bearing bottom plate, and a side wall within the enclosure frame is provided with a vertical inverted-L-shaped hook-like portion.

4. The cryogenic tissue sample embedding storage system of claim 3, wherein both the enclosure frame and the bearing bottom plate are square; the label cover is a square barrel, the upper end of the square barrel is a roof, and the roof is provided with a through hole.

5. The cryogenic tissue sample embedding storage system of claim 3, wherein the bearing bottom plate is provided with an upright column, and the upper end of the upright column is provided with a hook-like portion which is horizontally bent.

6. The cryogenic tissue sample embedding storage system of claim 3, wherein the bearing bottom plate is flexibly connected to the enclosure frame, and one side of the bearing bottom plate is connected to the enclosure frame through an elastic strip; the bearing bottom plate is provided with a connection plug column, and the lower end of the enclosure frame is provided with a first connection plug hole corresponding to the connection plug column.

7. The cryogenic tissue sample embedding storage system of claim 1, wherein there are a plurality of groove structures, which are evenly distributed horizontally; and the groove structure is a vertical square groove with one side open.

8. The cryogenic tissue sample embedding storage system of claim 1, wherein the embedding enclosure wall comprises comb-like bodies that are disposed oppositely, and an intersecting portion of the two comb-like bodies forms an embedding limiting area; the comb-like body is provided with a vertical through hole, a connection plug rod is inserted in the vertical through hole, and the embedding base is provided with a second connection plug hole corresponding to the lower end of the connection plug rod; and the lower end of the embedding enclosure wall is provided with a prying gap.

9. The cryogenic tissue sample embedding storage system of claim 1, wherein the embedding base is provided with a cooling ventilation duct; and the embedding base and embedding enclosure wall utilize heat-conducting metal.

* * * * *